(12) United States Patent
Kim et al.

(10) Patent No.: US 10,570,220 B2
(45) Date of Patent: Feb. 25, 2020

(54) COMPOSITION FOR DISPLAY SEALING MATERIAL, ORGANIC PROTECTION LAYER COMPRISING SAME, AND DISPLAY DEVICE COMPRISING SAME

(71) Applicant: SAMSUNG SDI CO., LTD., Yongin-si, Gyeonggi-do (KR)

(72) Inventors: Hye Jin Kim, Uiwang-si (KR); Mi Sun Kim, Uiwang-si (KR); Seong Ryong Nam, Uiwang-si (KR); Sung Min Ko, Uiwang-si (KR); Ji Yeon Lee, Uiwang-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 0 days.

(21) Appl. No.: 15/512,869

(22) PCT Filed: Apr. 10, 2015

(86) PCT No.: PCT/KR2015/003614
§ 371 (c)(1),
(2) Date: Mar. 21, 2017

(87) PCT Pub. No.: WO2016/068414
PCT Pub. Date: May 6, 2016

(65) Prior Publication Data
US 2017/0298164 A1 Oct. 19, 2017

(30) Foreign Application Priority Data

Oct. 29, 2014 (KR) ........................ 10-2014-0148655
Apr. 9, 2015 (KR) ........................ 10-2015-0050505

(51) Int. Cl.
*H01L 33/56* (2010.01)
*C08F 222/10* (2006.01)
(Continued)

(52) U.S. Cl.
CPC ................ *C08F 2/50* (2013.01); *C07C 69/54* (2013.01); *C07C 323/19* (2013.01);
(Continued)

(58) Field of Classification Search
CPC ..... C07C 323/19; C07C 69/54; C08F 220/30; C08F 220/34; C08F 2220/301;
(Continued)

(56) References Cited

U.S. PATENT DOCUMENTS

| 2011/0077334 A1* | 3/2011 | Oi ........................ C08F 220/36 524/264 |
| 2013/0171438 A1* | 7/2013 | Hayashi .................... C08F 2/44 428/220 |
| 2016/0126431 A1* | 5/2016 | Marukawa ............. C08G 59/68 257/100 |

FOREIGN PATENT DOCUMENTS

| CN | 101367893 A | 2/2009 |
| JP | 2009-256493 A | 11/2009 |

(Continued)

OTHER PUBLICATIONS

International Search Report dated Jun. 30, 2015 for PCT/KR2015/003614.
(Continued)

*Primary Examiner* — Matthew L Reames
*Assistant Examiner* — Benjamin T Liu
(74) *Attorney, Agent, or Firm* — Lee IP Law, PC

(57) ABSTRACT

The present invention relates to a composition for a display sealing material having a photopolymerization initiator and a photocurable monomer, the photocurable monomer comprising: a monomer not having the aromatic hydrocarbon group; and a monomer having two or more substituted or unsubstituted phenyl groups of chemical formula 1, wherein about 5 wt % to about 45 wt % of the monomer having two
(Continued)

or more substituted or unsubstituted phenyl groups is comprised on the basis of the photocurable monomer and about 55 wt % to about 95 wt % of the monomer not having the aromatic hydrocarbon group is comprised on the basis of the photocurable monomer.

15 Claims, 1 Drawing Sheet

(51) Int. Cl.

| | | |
|---|---|---|
| *C08F 2/50* | (2006.01) | |
| *H01L 51/00* | (2006.01) | |
| *C07C 69/54* | (2006.01) | |
| *C07C 323/19* | (2006.01) | |
| *C08F 220/30* | (2006.01) | |
| *C08F 220/34* | (2006.01) | |
| *C09D 133/08* | (2006.01) | |
| *C09D 133/14* | (2006.01) | |
| *C09D 135/02* | (2006.01) | |
| *H01L 51/52* | (2006.01) | |

(52) U.S. Cl.
CPC .......... *C08F 220/30* (2013.01); *C08F 220/34* (2013.01); *C08F 222/1006* (2013.01); *C09D 133/08* (2013.01); *C09D 133/14* (2013.01); *C09D 135/02* (2013.01); *H01L 33/56* (2013.01); *H01L 51/004* (2013.01); *C08F 2220/301* (2013.01); *C08F 2222/102* (2013.01); *C08F 2222/1013* (2013.01); *C08F 2800/20* (2013.01); *H01L 51/5253* (2013.01); *H01L 2251/301* (2013.01); *H01L 2251/303* (2013.01)

(58) Field of Classification Search
CPC ........ C08F 2222/1013; C08F 2222/102; C08F 222/1006; C08F 2800/20; C08F 2/50; C09D 133/08; C09D 133/14; C09D 135/02; H01L 33/56; H01L 51/004; H01L 2251/303; H01L 51/5253; H01L 2251/301
See application file for complete search history.

(56) References Cited

FOREIGN PATENT DOCUMENTS

| | | | |
|---|---|---|---|
| JP | 2010-030290 | A | 2/2010 |
| JP | 2010-234791 | A | 10/2010 |
| JP | 2011-051340 | A | 3/2011 |
| JP | 2013-067109 | A | 4/2013 |
| JP | 2014-193970 | * | 10/2014 |
| JP | 2014-193970 | A | 10/2014 |
| KR | 10-2009-0069136 | A | 6/2009 |
| KR | 10-2011-0071039 | A | 6/2011 |
| KR | 10-2013-0132639 | A | 12/2013 |
| KR | 10-2014-0046924 | A | 4/2014 |
| KR | 10-2014-0076424 | A | 6/2014 |
| KR | 10-1402355 | B1 | 6/2014 |
| KR | 10-2014-0140769 | A | 12/2014 |
| WO | WO 2008/053931 | A1 | 5/2008 |
| WO | WO 2013/077358 | A1 | 5/2013 |
| WO | WO 2013/165637 | A1 | 11/2013 |

OTHER PUBLICATIONS

Office Action dated Mar. 5, 2019 in the corresponding Japanese Patent Application No. 2017-523239.
Office Action dated Aug. 2, 2019 in the corresponding Chinese Patent Application No. 201580057390.9.

* cited by examiner

[Figure 1]
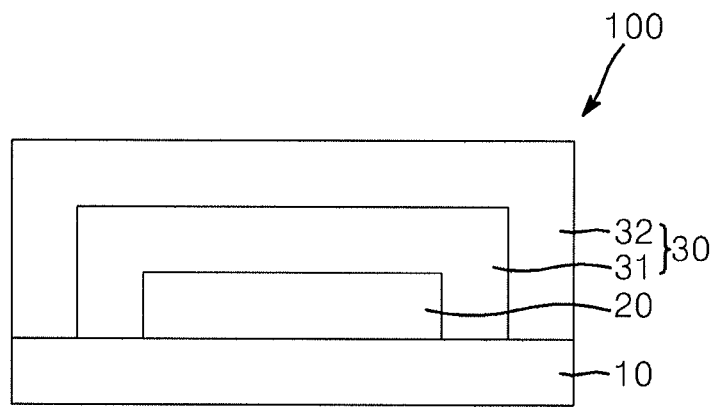
[Figure 2]
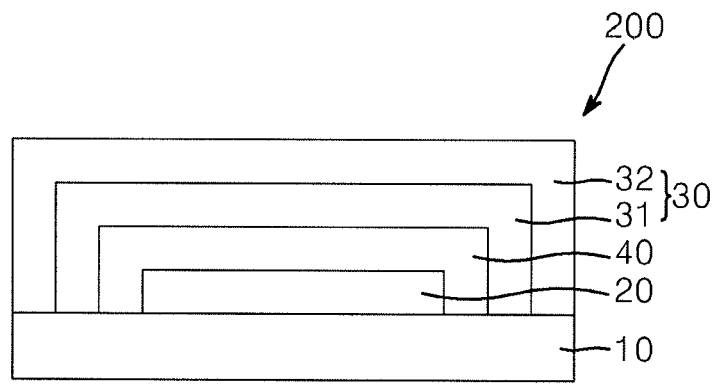

COMPOSITION FOR DISPLAY SEALING MATERIAL, ORGANIC PROTECTION LAYER COMPRISING SAME, AND DISPLAY DEVICE COMPRISING SAME

CROSS REFERENCE TO RELATED APPLICATIONS

This is the U.S. national phase application based on PCT Application No. PCT/KR2015/003614, filed Apr. 10, 2017, which is based on Korean Patent Application No. 10-2014-0148655, filed Oct. 29, 2014, and Korean Patent Application No. 10-2015-0050505, filed Apr. 9, 2015, the entire contents of all of which are hereby incorporated by reference.

TECHNICAL FIELD

The present invention relates to a composition for display sealing material, an organic protection layer including the same, and a display device including the same.

BACKGROUND ART

Organic electroluminescent devices used in optical display apparatuses can suffer from degradation or deterioration in properties by the environments such as moistures or gases. Specifically, the interface between a metal field and an organic emitting layer will be delaminated owing to moistures. Furthermore, high resistance will occur due to the oxidation of the metal, and organic materials themselves will be deteriorated by moistures or oxygen. Moreover, the organic materials and electrode materials will experience the oxidation by outgases from external or internal environments, and the organic electroluminescent device may have reduced luminous properties. Thus, the organic electroluminescent device must be encapsulated with an encapsulating composition to protect it from moistures or oxygen.

The organic electroluminescent device has been encapsulated in a multilayer structure in which a inorganic protection layer and an organic protection layer are formed. The inorganic protection layer may be formed by a plasma deposition process, which can cause the organic protection layer to be etched by plasma. When the organic protection layer is etched, the encapsulating function of the organic protection layer can be damaged. Thus, the organic light emitting device can suffer from deterioration in luminous properties and reliability.

In this regard, the background of the present invention is disclosed in Korean Laid-Open Patent Publication No. 2011-0071039 A (LG Display).

DISCLOSURE

Technical Problem

In one aspect, the present invention provides a composition for display sealing material realizing an organic protection layer having high plasma resistance.

In another aspect, the present invention provides a composition for display sealing material realizing an organic protection layer having remarkably low moisture permeation and oxygen permeability.

In still another aspect, the present invention provides a composition for display sealing material realizing an organic protection layer having excellent transparency.

In still another aspect, the present invention provides a composition for display sealing material realizing an organic protection layer having low surface roughness leading to high surface smoothness.

In still another aspect, the present invention provides a composition for display sealing material realizing an organic protection layer protecting the apparatus from the environments including moistures and gases to provide the apparatus with time-dependent reliability.

In still another aspect, the present invention provides a display apparatus including a cured product of a composition for display sealing material.

Technical Solution

In one aspect of the present invention, a composition for display sealing material may include a photo-curable monomer and a photopolymerization initiator, wherein the photo-curable monomer may include a monomer not containing an aromatic hydrocarbon group; and a monomer containing two or more of substituted or unsubstituted phenyl groups, represented by Formula 1, and the monomer containing two or more of substituted or unsubstituted phenyl groups may be present in an amount of from about 5 wt % to about 45 wt % in the photo-curable monomer, and the monomer not containing the aromatic hydrocarbon group may be present in an amount of from about 55 wt % to about 95 wt % in the photo-curable monomer.

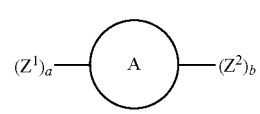

<Formula 1>

(wherein A is a hydrocarbon having two or more of substituted or unsubstituted phenyl groups, or a hydrocarbon having a heteroatom and two or more of substituted or unsubstituted phenyl groups;

Z1 and Z2 are each independently represented by Formula 2; and a and b are an inter of 0 to 2, respectively, and a+b is an inter of 1 to 4)

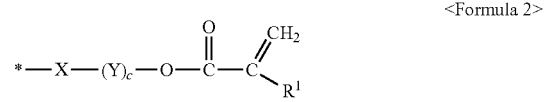

<Formula 2>

(wherein * represents a linker site to a carbon atom on A;

X is a single bond, O, or S;

Y is a substituted or unsubstituted C1 to C10 linear alkylene group, or a substituted or unsubstituted C1 to C20 alkoxy group;

R1 is a hydrogen or a C1 to C5 alkyl group; and c is 0 or 1.

In still another aspect of the present invention, a display apparatus may include a display member, and a composite protection layer formed on the display member, wherein the composite protection layer may include a inorganic protection layer and an organic protection layer, and the organic protection layer includes a cured product prepared of the composition for display sealing material.

Advantageous Effects

The composition of the present invention may realize an organic protection layer having high plasma resistance.

The composition of the present invention may realize an organic protection layer having remarkably low moisture permeation and oxygen permeability.

The composition of the present invention may realize an organic protection layer having excellent transparency.

The composition of the present invention may realize an organic protection layer having low surface roughness leading to high surface smoothness.

The composition of the present invention may realize an organic protection layer protecting the apparatus from the environments including moistures and gases to provide the apparatus with time-dependent reliability.

DESCRIPTION OF DRAWINGS

FIG. 1 is a cross-sectional view of a display apparatus according to one embodiment of the present invention.

FIG. 2 is a cross-sectional view of a display apparatus according to another embodiment of the present invention.

BEST MODE

Embodiments of the present invention will now be described in detail. It should be understood that the present invention is not limited to the following embodiments and may be embodied in different ways. Although some parts of elements is described for the convenience of the description, those skilled in the art readily may understand the other parts of elements. In the drawings, width and thickness of the elements can be expressed in a magnified form and some of irrelevant elements can be omitted for clarity. In addition, the spirits of the present invention may be embodied in various other forms by those skilled in the art without departing the technical sprits of the present invention.

As used herein, terms such as "upper" and "lower" are defined with reference to the accompanying drawings. Thus, it will be understood that the term "upper surface" can be used interchangeably with the term "lower surface." The term "on" encompasses both that one element is disposed "directly on" another structure, and that the other structure can be interposed. Meanwhile, the term "directly on" means that the other structure is not interposed.

As used herein, the term "(meth)acryl" refers to an acryl and/or a methacryl.

As used herein, the term "substituted", unless otherwise stated, means that at least one hydrogen atom among functional groups is substituted with a hydroxyl group, a nitro group, an imino group (=NH, =NR, wherein R is a C1 to C10 alkyl group), an amidino group, a hydrazine or a hydrazone group, a carboxyl group, a C1 to C20 alkyl group, a C6 to C30 aryl group, a C3 to C30 heteroaryl group, or a C2 to C30 heterocycloalkyl group.

As used herein, the term "heteroatom" means any atom selected from a group of consisting of N, O, S and P, and the term "hetero" means that a carbon atom is substituted with any one atom selected from a group of consisting of N, O, S and P.

As used herein, the "plasma resistance" may be determined depending on the etching rate to be etched when a cured product of an encapsulating composition is subjected to a plasma treatment. Lower etching rate represents higher plasma resistance.

As used herein, the "alkylene group" means a alkanediyl group attached via a saturated hydrocarbon without a double bond between (meth)acrylates at each terminal. Furthermore, the number of the carbon atom of the alkylene group means the number of the carbon atom of the alkylene group itself except the carbon atom in the di(meth)acrylate group.

In one aspect of the present invention, a composition for display sealing material may include a photo-curable monomer and a photopolymerization initiator.

The photo-curable monomer means a photo-curable monomer capable of curing reaction by a photopolymerization initiator. A non-silicon monomer not containing a silicon (Si) atom may be used as the photo-curable monomer. For example, it may be, but not limited to, a monomer consisted of an element selected from C, H, O, N and S. The photo-curable monomer may be synthesized by a typical synthesis method, or be a commercially available product.

Specifically, the composition for display sealing material according to one aspect of the present invention may include a photo-curable monomer and a photopolymerization initiator, and the photo-curable monomer may include a monomer not containing an aromatic hydrocarbon group; and a monomer containing two or more of substituted or unsubstituted phenyl groups represented by Formula 1, and about 5 wt % to about 45 wt % of the monomer containing two or more of substituted or unsubstituted phenyl groups in the photo-curable monomer and about 55 wt % to about 95 wt % of the monomer not containing the aromatic hydrocarbon group in the photo-curable monomer.

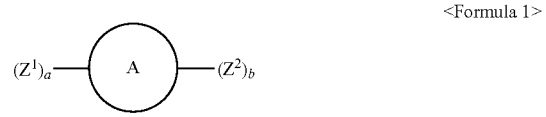

<Formula 1> wherein A is a hydrocarbon having two or more of substituted or unsubstituted phenyl groups, or a hydrocarbon having a heteroatom and two or more of substituted or unsubstituted phenyl groups, Z1 and Z2 are each independently represented by Formula 2, and a and b are an inter of 0 to 2, respectively, and a+b is an inter of 1 to 4.

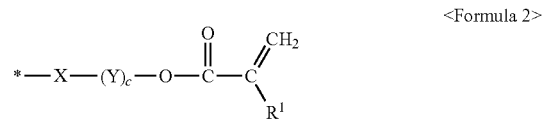

<Formula 2> wherein * represents a linker site to a carbon atom on A;
X is a single bond, O, or S;
Y is a substituted or unsubstituted C1 to C10 linear alkylene group, or substituted or unsubstituted C1 to C20 alkoxy group,
$R^1$ is a hydrogen or a C1 to C5 alkyl group; and c is 0 or 1.

In the formula, A is a hydrocarbon having two or more of substituted or unsubstituted phenyl groups, or a hydrocarbon having a heteroatom and two or more of substituted or unsubstituted phenyl groups. The hydrocarbon having two or more of substituted or unsubstituted phenyl groups, or a hydrocarbon having a heteroatom and two or more of substituted or unsubstituted phenyl groups means a hydrocarbon in which two or more of substituted or unsubstituted phenyl groups are not condensed but linked via a single bond, an oxygen atom, a sulfur atom, a substituted or unsubstituted C1 to C5 alkyl group, a C3 to C6 alkylene group unsubstituted or substituted with a heteroatom, an ethenylene group, an ethynylene group, or a carbonyl group. For example, the hydrocarbon having two or more of phenyl groups, or a hydrocarbon having a heteroatom and two or more of substituted or unsubstituted phenyl groups may include, but not limited to, a substituted or unsubstituted biphenyl group, a substituted or unsubstituted triphenylmethyl group, a substituted or unsubstituted terphenyl group, a substituted or unsubstituted biphenylene group, a substituted or unsubstituted terphenylene group, a substituted or unsubstituted quaterphenylene group, a substituted or unsubstituted 2-phenyl-2-(phenylthio)ethyl group, a substituted or unsubstituted 2,2-diphenylpropane group, a substituted or unsubstituted diphenylmethane group, a substituted or unsubstituted cumyl phenyl group, a substituted or unsubstituted bisphenol F group, a substituted or unsubstituted bisphenol A group, a substituted or unsubstituted biphenyloxy group, a substituted or unsubstituted terphenyloxy group, a substituted or unsubstituted quaterphenyloxy group, a substituted or unsubstituted quinquephenyloxy group, structural isomers thereof, and the like.

The monomer containing two or more of substituted or unsubstituted phenyl groups may be prepared from mono (meth)acrylate, di(meth)acrylate or mixtures thereof. And the examples of the monomer containing two or more of substituted or unsubstituted phenyl groups include, but not limited to, 4-(meth)acryloxy-2-hydroxybenzophenone, ethyl-3,3-diphenyl(meth)acrylate, benzoyloxyphenyl (meth)acrylate, bisphenol A di(meth)acrylate, ethoxylated bisphenol A di(meth)acrylate, bisphenol F di(meth)acrylate, ethoxylated bisphenol F di(meth)acrylate, 4-cumylphenoxyethylacrylate, ethoxylated bisphenylfluorene diacrylate, 2-phenylphenoxyethyl (meth)acrylate, 2,2'-phenylphenoxyethyl di(meth)acrylate, 2-phenylphenoxypropyl(meth)acrylate, 2,2'-phenylphenoxypropyl di(meth)acrylate, 2-phenylphenoxybutyl(meth)acrylate, 2,2'-phenylphenoxybutyl di(meth)acrylate, 2-(3-phenylphenyl)ethyl (meth)acrylate, 2-(4-benzylphenyl)ethyl (meth)acrylate, 2-phenyl-2-(phenylthio)ethyl (meth)acrylate, 2-(triphenylmethyloxy)ethyl (meth)acrylate, 4-(triphenylmethyloxy)butyl(meth)acrylate, 3-(biphenyl-2-yloxy)butyl(meth)acrylate, 2-(biphenyl-2-yloxy)butyl(meth)acrylate, 4-(biphenyl-2-yloxy)propyl (meth)acrylate, 3-(biphenyl-2-yloxy)propyl(meth)acrylate, 2-(biphenyl-2-yloxy)propyl(meth)acrylate, 4-(biphenyl-2-yloxy)ethyl(meth)acrylate, 3-(biphenyl-2-yloxy)ethyl (meth)acrylate, 2-(4-benzylphenyl)ethyl(meth)acrylate, 4,4'-di(acryloyloxymethyl)biphenyl, 2,2'-di(acryloyloxyethoxy)biphenyl, structural isomers thereof, or mixtures thereof. In addition, the (meth)acrylate described herein is constructed only as the examples, and not limited thereto, and further includes all the acrylate related to the structural isomers. For example, although 2,2'-phenylphenoxyethyl di(meth)acrylate is described as one example, the present invention encompasses 3,2'-phenylphenoxyethyl di(meth)acrylate, 3,3'-phenylphenoxyethyl di(meth)acrylate, and the like corresponding to its structural isomer.

In one embodiment, the monomer containing two or more of phenyl groups may be a mono(meth)acrylate of Formula 3.

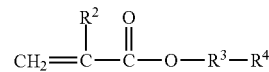
<Formula 3> wherein, $R^2$ is hydrogen or a methyl group, $R^3$ is a substituted or unsubstituted linear C1 to C10 alkylene group or a substituted or unsubstituted C1 to C20 alkoxy group, and $R^4$ is a hydrocarbon having two or more of substituted or unsubstituted phenyl groups, or a hydrocarbon having a heteroatom and two or more of substituted or unsubstituted phenyl groups.

For example, the hydrocarbon having two or more of substituted or unsubstituted phenyl groups, or a hydrocarbon having a heteroatom and two or more of substituted or unsubstituted phenyl groups means a hydrocarbon in which two or more of substituted or unsubstituted phenyl groups are not condensed but linked via a single bond, an oxygen atom, a sulfur atom, a substituted or unsubstituted C1 to C3 alkyl group, a C3 to C6 alkylene group unsubstituted or substituted with a heteroatom, an ethenylene group, an ethynylene group, or a carbonyl group. For example, the hydrocarbon having two or more of phenyl groups, or a hydrocarbon having a heteroatom and two or more of substituted or unsubstituted phenyl groups may include, but not limited to, a substituted or unsubstituted biphenyl group, a substituted or unsubstituted triphenylmethyl group, a substituted or unsubstituted terphenyl group, a substituted or unsubstituted biphenylene group, a substituted or unsubstituted terphenylene group, a substituted or unsubstituted quaterphenylene group, a substituted or unsubstituted 2-phenyl-2-(phenylthio)ethyl group, a substituted or unsubstituted 2,2-diphenylpropane group, a substituted or unsubstituted diphenylmethane group, a substituted or unsubstituted cumyl phenyl group, a substituted or unsubstituted bisphenol F group, a substituted or unsubstituted bisphenol A group, a substituted or unsubstituted biphenyloxy group, a substituted or unsubstituted terphenyloxy group, a substituted or unsubstituted quaterphenyloxy group, a substituted or unsubstituted quinquephenyloxy group, and the like.

In one embodiment, the monomer containing two or more of phenyl groups may be a di(meth)acrylate of Formula 4.

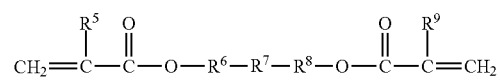
<Formula 4> wherein, $R^5$ and $R^9$ are hydrogen or a methyl group, $R^6$ and $R^8$ are each independently a substituted or unsubstituted linear C1 to C10 alkylene group, or —R'O-(wherein R' is a substituted or unsubstituted linear $C_1$ to $C_{10}$ alkylene group), and $R^7$ is a hydrocarbon having two or more of substituted or unsubstituted phenyl groups, or a hydrocarbon having a heteroatom and two or more of substituted or unsubstituted phenyl groups For example, the hydrocarbon having two or more of substituted or unsubstituted phenyl groups, or a hydrocarbon having a heteroatom and two or more of substituted or unsubstituted phenyl groups means a hydrocarbon in which two or more of substituted or unsubstituted phenyl groups are not condensed but linked via a single bond, an oxygen atom, a sulfur atom, a substituted or unsubstituted C1 to C4 alkyl group, a C3 to C6 alkylene group unsubstituted or substituted with a heteroatom, an ethenylene group, an ethynylene group, or a carbonyl group. For example, the hydrocarbon may include, but not limited to, a substituted or unsubstituted biphenylene group, a substituted or unsubstituted triphenylmethylene group, a substituted or unsubstituted terphenylene group, a substituted or unsubstituted quaterphenylene group, 2-phenyl-2-(phenylthio)ethylene group, 2,2-diphenylpropylene group, diphenylmethylene group, and the like.

In the formula 1, a and b are independently an integer of 0 to 2, and a+b is an integer of 1 to 4, and in one embodiment an integer of 1 or 2.

The monomer containing two or more of substituted or unsubstituted phenyl groups may have a weight average molecular weight of about 100 g/mol or more and about 1000 g/mol or less, particularly about 130 g/mol or more and about 700 g/mol or less, and more particularly about 150 g/mol or more and about 600 g/mol or less.

Within this range, it is possible to provide an encapsulant with high plasma resistance, low surface roughness, and improved transmittance.

The monomer containing two or more of substituted or unsubstituted phenyl groups may be present in an amount of from about 5 wt % to about 45 wt %, and in particular from about 10 wt % to about 40 wt % in total weight of the photo-curable monomer. Within this range, it is possible to achieve a viscosity suitable for forming the encapsulant and excellent plasma resistance.

The photo-curable monomer may include a monomer not containing the aromatic hydrocarbon group.

The monomer not containing the aromatic hydrocarbon group may not contain the aromatic hydrocarbon group, and comprise the monomer may have 1 to 20 groups selected from a vinyl group, an acryl group and a methacryl group as the photo-curable functional group. The monomer not containing the aromatic hydrocarbon group may not contain the aromatic hydrocarbon group, specifically 1 to 6 groups, for example, 1 to 3, 1 to 2, 1, or 2 groups selected from a vinyl group, an acryl group and a methacryl group as the photo-curable functional group.

According to the present invention, the monomer not containing the aromatic hydrocarbon group may have a weight average molecular weight of about 100 g/mol or more and about 500 g/mol or less, particularly, about 130 g/mol or more and about 400 g/mol or less, and more particularly about 200 g/mol or more and about 300 g/mol or less. In this range of the weight average molecular weight of the monomer, the process may have an advantageous effect.

The monomer not containing the aromatic hydrocarbon group may include a mono-functional monomer, a multi-functional monomer, or mixtures thereof, which have the photo-curable functional group.

Specifically, the monomer not containing the aromatic hydrocarbon group may be (meth)acrylate monomer. And the monomer not containing the aromatic hydrocarbon group may include, for example, an unsaturated carbonic acid ester having a C1 to C20 alkyl group, a C3 to C20 cycloalkyl group, or a hydroxyl group and a C1 to C20 alkyl group; an unsaturated carbonic acid ester having a C1 to C20 amino alkyl group; a C1 to C20 saturated or unsaturated vinyl ester of carbonic acid; a vinyl cyanide compound; an unsaturated amide compound; a mono-functional or multi-functional (meth)acrylate of a monovalent alcohol or mutivalent alcohol, and the like. The "multivalent alcohol" means an alcohol having two or more hydroxyl groups, and in particular, an alcohol having 2 to 20 hydroxyl groups, preferably 2 to 10 hydroxyl groups, and more preferably 2 to 6 hydroxyl groups.

In one embodiment, the (meth)acrylate monomer not containing the aromatic hydrocarbon group among the monomer not containing the aromatic hydrocarbon group may be a mono (meth)acrylate, a di(meth)acrylate, a tri (meth)acrylate, a tetra (meth)acrylate, and the like having a substituted or unsubstituted C1 to C20 alkyl group, a substituted or unsubstituted C1 to C20 alkyl silyl group, a substituted or unsubstituted C3 to C20 cycloalkyl group, a substituted or unsubstituted C1 to C20 alkylene group, amine group, ethyleneoxide group, and the like Specifically, it may include, but not limited to, an unsaturated carbonic acid ester including (meth)acrylic acid ester such as methyl (meth)acrylate, ethyl (meth)acrylate, butyl (meth)acrylate, 2-hydroxyethyl (meth)acrylate, 2-hydroxybutyl (meth)acrylate, hexyl (meth)acrylate, octyl (meth)acrylate, nonyl (meth)acrylate, decanyl (meth)acrylate, undecanyl (meth)acrylate, dodecyl (meth)acrylate, cyclohexyl (meth)acrylate, and the like; an unsaturated carbonic acid aminoalkyl ester such as 2-aminoethyl (meth)acrylate, 2-dimethylaminoethyl (meth)acrylate, and the like; a saturated or unsaturated carbonic acid vinyl ester such as vinyl acetate, and the like; vinyl cyanide compounds such as (meth)acrylonitrile, and the like; an unsaturated amide compounds such as (meth)acrylamide, and the like; ethylene glycol di(meth)acrylate, triethylene glycol di(meth)acrylate, trimethylolpropane tri(meth)acrylate, 1,4-butanediol di(meth)acrylate, 1,6-hexanediol di(meth)acrylate, octanediol di(meth)acrylate, nonanediol di(meth)acrylate, decanediol di(meth)acrylate, undecanediol di(meth)acrylate, dodecanediol di(meth)acrylate, neopentylglycol di(meth)acrylate, pentaerythritol di(meth)acrylate, pentaerythritol tri(meth)acrylate, pentaerythritol tetra(meth)acrylate, dipentaerythritol di(meth)acrylate, dipentaerythritol tri(meth)acrylate, dipentaerythritol tetra(meth)acrylate, dipentaerythritol penta (meth)acrylate, dipentaerythritol hexa(meth)acrylate, or mixtures thereof.

In one embodiment, the monomer not containing an aromatic hydrocarbon group may include, as a non-aromatic compound not having an aromatic group, at least one of a mono(meth)acrylate having C1 to C20 alkyl group, a mono (meth)acrylate having amine group, a di(meth)acrylate having a substituted or unsubstituted C1 to C20 alkylene group, a di(meth)acrylate having ethylene oxide group, and a tri(meth)acrylate having ethylene oxide group.

The mono(meth)acrylate having the substituted or unsubstituted C1 to C20 alkyl group may include specifically, but not limited to, decyl (meth)acrylate, undecyl (meth)acrylate, lauryl (meth)acrylate, tridecyl (meth)acrylate, tetradecyl (meth)acrylate, pentadecyl (meth)acrylate, hexadecyl (meth)acrylate, heptadecyl (meth)acrylate, octadecyl (meth)acrylate, nonadecyl (meth)acrylate, arachidyl (meth)acrylate, or mixtures thereof.

The mono(meth)acrylate having the amine group may include, but not limited to, 2-aminoethyl (meth)acrylate, 2-dimethylaminoethyl (meth)acrylate or mixtures thereof.

The di(meth)acrylate having the substituted or unsubstituted C1 to C20 alkylene group may be, for example, di(meth)acrylate having C1 to C20 alkylene group, or non-silicone-based di(meth)acrylate having substituted or unsubstituted long-chain alkylene group. If the encapsulating composition includes the nonsilicone-based di(meth)acrylate having long-chain alkylene group, the composition may be used to form easily an organic barrier layer on an organic light emitting device or an inorganic layer encapsulating the organic light emitting device by a deposition etc. The di(meth)acrylate having the substituted or unsubstituted C1 to C20 alkylene group may include, for example, but not limited to, octanediol di(meth)acrylate, nonanediol di(meth)acrylate, decanediol di(meth)acrylate, undecanediol di(meth)acrylate, dodecanediol di(meth)acrylate, or mixtures thereof. If the encapsulating composition may include a substituted or unsubstituted C1 to C20 alkylene group, the composition may have excellent photopolymerization rate and low viscosity.

The di(meth)acrylate or tri(meth) acrylate having the ethylene oxide group may include specifically, but not limited to, ethylene glycol di(meth)acrylate, triethylene glycol di(meth)acrylate, trimethylolpropane tri(meth)acrylate, or mixtures thereof.

The monomer not containing the aromatic hydrocarbon group may be present in an amount of from about 55 wt % to about 95 wt %, and in particular, from about 60 wt % to about 90 wt % in total weight of the photo-curable monomer. Within this range, it is possible to achieve a viscosity of the composition for display sealing material suitable for forming the encapsulant of the organic electroluminescent device.

The photopolymerization initiator may include, without limitation, a typical photopolymerization initiator capable of photo-curing reaction. For example, the photopolymerization initiator may include triazine, acetophenone, benzophenone, thioxanthone, benzoin, phosphorus, oxime, or mixtures thereof.

The triazine initiator may include, for example, 2,4,6-trichloro-s-triazine, 2-phenyl-4,6-bis(trichloromethyl)-s-triazine, 2-(3',4'-dimethoxy styryl)-4,6-bis(trichloromethyl)-s-triazine, 2-(4'-methoxy napthyl)-4,6-bis(trichloromethyl)-s-triazine, 2-(p-methoxy phenyl)-4,6-bis(trichloromethyl)-s-triazine, 2-(p-tollyl)-4,6-bis(trichloromethyl)-s-triazine, 2-biphenyl-4,6-bis(trichloromethyl)-s-triazine, bis(trichloromethyl)-6-styryl-s-triazine, 2-(naptho-1-yl)-4,6-bis(trichloromethyl)-s-triazine, 2-(4-methoxy naptho-1-yl)-4,6-bis(trichloromethyl)-s-triazine, 2,4-trichloromethyl(piperonyl)-6-triazine, 2,4-(trichloromethyl(4'-methoxy styryl)-6-triazine, or mixtures thereof.

The acetophenone initiator may include, for example, 2,2'-diethoxy acetophenone, 2,2'-dibutoxy acetophenone, 2-hydroxy-2-methyl propiophenone, p-t-butyl trichloro acetophenone, p-t-butyl dichloro acetophenone, 4-chloro acetophenone, 2,2'-dichloro-4-phenoxy acetophenone, 2-methyl-1-(4-(methylthio)phenyl)-2-morpholino propane-1-one, 2-benzyl-2-dimethyl amino-1-(4-morpholino phenyl)-butan-1-one, or mixtures thereof.

The benzophenone initiator may include, for example, benzophenone, benzoyl benzoic acid, benzoyl benzoic acid methyl ester, 4-phenyl benzophenone, hydroxy benzophenone, acrylated benzophenone, 4,4'-bis(dimethyl amino) benzophenone, 4,4'-dichlorobenzophenone. 3,3'-dimethyl-2-methoxy benzophenone, or mixtures thereof.

The thioxanthone initiator may include, for example, thioxanthone, 2-methyl thioxanthone, isopropyl thioxanthone, 2,4-diethyl thioxanthone, 2,4-diisopropyl thioxanthone, 2-chloro thioxanthone, or mixtures thereof.

The benzoin initiator may include, for example, benzoin, benzoin methyl ether, benzoin ethyl ether, benzoin isopropyl ether, benzoin isobutyl ether, benzyl dimethyl ketal, or mixtures thereof.

The phosphorus initiator may include, for example, bis benzoyl phenyl phosphine oxide, benzoyl diphenyl phosphine oxide, or mixtures thereof.

The oxime initiator may include, for example, 2-(o-benzoyloxime)-1-[4-(phenylthio)phenyl]-1,2-octanedione and 1-(o-acetyloxime)-1-[9-ethyl-6-(2-methylbenzoyl)-9H-carbazol-3-yl]ethanone, or mixtures thereof.

The photopolymerization initiator may be present in an amount of from about 0.1 parts by weight to about 20 parts by weight based on 100 parts by weight of the photo-curable monomer and the photopolymerization initiator in the composition for display sealing material. Within this range, the photo-curing may occur sufficiently upon exposure, and the decrease in transmittance owing to the unreacted initiator residing after photo-curing may be prevented. Specifically, the photopolymerization initiator may be present in an amount of about 0.5 to about 10 parts by weight, and in particular, from about 1 to about 8 parts by weight. In addition, the photopolymerization initiator may be present in an amount of from about 0.1 wt % to about 10 wt %, and in particular, about 0.1 wt % to about 8 wt %, on the solid contents, in the composition for display sealing material. Within this range, the photo-curing may occur sufficiently, and the decrease in transmittance owing to the unreacted residual initiator may be prevented.

Furthermore, instead of the photopolymerization initiator, the photo acid generator or the photopolymerization initiator such as cabazole, diketone, sulfonium, iodonium, diazo, biimidazole, and the like may be used.

In another embodiment of the present invention, the composition for display sealing material may further include an antioxidant.

The antioxidant may improve the thermal stability of the encapsulating layer. The antioxidant may include, but not limited to, at least one selected from the group consisting of phenol, quinone, amine and phosphite. For example, the antioxidant may include, for example, tetrakis[methylene(3,5-di-t-butyl-4-hydroxyhydrocinnamate)]methane, tris(2,4-di-tert-butylphenyl)phosphite, and the like.

The antioxidant may be present in an amount of from about 0.01 parts by weight to about 3 parts by weight, and in particular, about 0.01 parts by weight to about 1 part by weight in about 100 parts by weight of the photo-curable monomer and the photopolymerization initiator in the composition for display sealing material. Within this range, it is possible to achieve excellent thermal stability.

The composition for display sealing material according to other embodiment of the present invention may further include a thermal stabilizer. As a result, the composition for display sealing material according to other embodiment of the present invention may suppress the viscosity change at an ambient temperature. In addition, the composition may have high light transmittance and photopolymerization rate over the encapsulating composition not including thermal stabilizer, and low plasma etching rate. The composition is the same as the composition for display sealing material according to one embodiment of the present invention except that it further includes the thermal stabilizer. Hereinafter, details of the thermal stabilizer will be described.

The thermal stabilizer included in the composition serves to suppress the viscosity change of the composition at an ambient temperature, and may be any thermal stabilizer typically used. For example, the thermal stabilizer may include a sterically hindered phenolic thermal stabilizer. Specifically, the thermal stabilizer may include, but not limited to, at least one of poly(di-cyclopentadiene-co-p-cresol), octadecyl-3-(3,5-di-tert-butyl-4-hydroxyphenyl) propionate, 2,6-di-tert-butyl-4-methylphenol, 2,2'-methano-bi(4-methyl-6-tert-butyl-phenol), 6,6'-di-tert-butyl-2,2'-thiodi-p-cresol, tris(4-tert-butyl-3-hydroxy-2,6-dimethylbenzyl)isocyanurate, triethylneglycol-bis(3-tert-butyl-4-hydroxy-5-methylphenyl), 4,4'-thiobis(6-tert-butylm-cresol), 3,3'-bis(3,5-di-tert-butyl-4-hydroxyphenyl)-N,N'-hexamethylene-dipropionamide, pentaerythritol tetrakis (3-(3,5-di-tert-butyl-4-hydroxyphenyl)propionate, stearyl-3,5-di-tert-butyl-4-hydroxyphenylpropionate, pentaerythritoltetrakis 1,3,5-tris(2,6-di-methyl-3-hydroxy-4-tert-benzyl)isocyanurate, 1,3,5-tris(3,5-di-tert-butyl-4-hydroxybenzyl)isocyanurate, and 1,3,5-tris(2-hydroxyethyl) isocyanurate-tris(3,5-di-tert-butylhydroxyphenylpropionate).

The thermal stabilizer may be present in an amount of about 2000 ppm or less, for example, about 0.01 ppm to about 2000 ppm, for example, about 100 ppm to about 1000 ppm, on the solid contents, based on the total weight of the photo-curable monomer and the photopolymerization initiator in the composition for display sealing material. Within this range, the thermal stabilizer may improve storage stability and processability of the encapsulating composition in liquid phase.

The composition for display sealing material may be subjected to UV curing at a dose of about 10 mW/cm$^2$ to about 500 mW/cm$^2$ for about 1 to about 100 seconds.

The composition for display sealing material may have a plasma etching rate represented by Equation 1 of about 400 nm/min or less and a roughness of about 2 nm or less:

$$\text{Plasma etching rate(nm/min)}=(T0-T1)/M \quad \text{[Equation 1]}$$

Where in equation 1, T0 is a thickness (nm) of a sample prepared by applying the composition for display sealing material on a substrate by a spray, and UV curing at a dose of about 100 mW/cm$^2$ for about 10 seconds, T1 is a thickness (nm) of the prepared sample after being subjected to a plasma treatment under the conditions of ICP (inductively coupled plasma) power of 2500 W, RF (radio frequency) power of 300 W, DC bias of 200 V, argon (Ar) flow rate of 50 sccm, and pressure of 10 mTorr for about 1 min, each T0 and T1 are the thickness exclusive of the thickness of the substrate, and M is a time of the plasma treatment (min).

It is possible to provide the organic protection layer with remarkably low plasma etching rate, which represents the damage of the organic protection layer caused by the plasma treatment, using the photo-curable monomer having plasma etching rate after curing, when the organic protection layer is formed on the organic electroluminescent device or the inorganic protection layer formed on the organic electroluminescent device. In particular, the plasma etching rate may be about 400 nm/min or less, particularly about 10 nm/min to about 390 nm/min, and more particularly about 10 nm/min to about 385 nm/min. The plasma etching rate, represented by equation 1, of more than about 400 nm/min may lead to the increase in damage of the organic protection layer and the decrease in reliability of the device.

The surface roughness is a roughness of deposited surface, measured for its flection when the composition for display sealing material is deposited on the substrate. The lower surface roughness may attribute to the smoothness of the display.

The roughness used herein may be determined by the general method well known to those skilled in the art according to roughness measurements. For example, it may be determined using an atomic force microscope (AFM). According to the present invention, the surface roughness (roughness of the deposited surface), measured using AFM, may be preferably about 2 nm or less, and in particular from about 0 nm to about 2 nm, from about 0 nm to about 1.9 nm, from about 0 nm to about 1.85 nm. According to the present invention, if the surface roughness is about 2 nm or less, then it is possible to provide the organic protection layer with the smooth surface and the inorganic protection layer with the smooth surface after depositing the organic protection layer. If the surface roughness is more than about 2 nm, then the organic protection layer may be provided with the unsmooth surface, and when the inorganic protection layer is deposited on the surface of the cured product, the inorganic protection layer may be easily broken.

The generated amount of the outgases may be about 2000 ppm or less in the display apparatus including the organic protection layer formed from the composition for display sealing material. Within this range, it is possible to increase the reliability since the element of the apparatus has long self-life. Specifically, the amount may be about 10 ppm to about 1000 ppm.

The generated amount of the outgases may be determined by a typical method. For example, the composition for display sealing material may be applied on the glass substrate, and subjected to UV curing at a dose of about 100 mW/cm$^2$ for about 10 seconds to prepare a cured specimen having a about 5 μm thick film. A TD-GC/MS (TD: JTD505III, GC/MS: Clarus 600, Perkin Elmer) equipment may be used to determine the amount of the outgas captured on certain area (1×5 cm$^2$), generated by heating the 5 μm thick film from about 40° C. to about 320° C. at a rate of about 10° C./min.

The composition for display sealing material may have a color coordinate YI (ASTM D1925) of about 0.5 or less, and in particular, from about 0.1 to about 0.5 after curing. Within this range, the encapsulant of the display may be transparent, and transmit a light similar to a white light and thus applied to the display.

The color coordinate may be determined by a typical method. For example, the composition for display sealing material may be applied on the glass substrate, and subjected to UV curing at a dose of about 100 mW/cm$^2$ for about 10 seconds to prepare a cured specimen having a about 5 μm thick film. A UV-visible spectrophotometer (UV-2450, SHIMADZU) analysis equipment may be used to determine the transmittance of the about 5 μm thick film at a wavelength of 300 nm to 800 nm and calculate the color coordinate YI (ASTM D1925).

The composition for display sealing material may have a total transmittance of about 90% or more and about 100% or less, and in particular, 95% or more and 100% or less after curing, and thus provide the transparent organic protection layer.

The total transmittance and a haze may be determined using a hazemeter (NDH-5000, Nippon Denshoku) at a wavelength of about 400 nm to about 700 nm according to ASTM D1003-95 5.

The composition for display sealing material may be applied to the front side to be emitted, and should not exhibit any color and be transparent. If the encapsulant of the display exhibit any color, the light generated from the light source of the display penetrates the encapsulant positioned in the front side and then leads to the distortion of the color to be realized because the color coordinate is discrepant. Furthermore, if the transparency is lower, the light emitted to the front side may have reduced efficacy and reduce the sharpness of the display.

In some embodiments of the present invention, the composition for display sealing material may be used as the encapsulant of the organic electroluminescent device. Specifically, the organic electroluminescent device may be damaged from the surrounding environments, for example, liquids or gases, particularly moistures or oxygen, or chemicals used in the process of preparing the apparatus including the organic electroluminescent device. Furthermore, to prevent the deterioration of the properties, the composition may be used as the encapsulant for forming the organic protection layer to prevent the organic electroluminescent device from the surrounding environments.

In some embodiments of the present invention, the composition for display sealing material may be used as the encapsulant of the device member. Specifically, the device member may be damaged from the surrounding environments, for example, liquids or gases, particularly moistures or oxygen, or chemicals used in the process of preparing the apparatus including the organic electroluminescent device. Furthermore, to prevent the deterioration of the properties, the composition may be used as the encapsulant for forming the organic protection layer to prevent the device member from the surrounding environments. The device member may include, for example, a flexible organic electroluminescent device, an organic electroluminescent device, and the like.

In some embodiments of the present invention, the composition for display sealing material may be used to form the organic protection layer formed on the organic electroluminescent device, or the organic protection layer formed on the inorganic protection layer formed on the organic electroluminescent device. The organic protection layer may be formed by, but not limited to, a deposition, an ink jet, and the like.

According to still another aspect of the present invention, a display apparatus may include a device member, and a composite protection layer formed on the device member, wherein the composite protection layer may include a inorganic protection layer and an organic protection layer, and the organic protection layer may be prepared of a composition for display sealing material according to some aspects of the present invention.

Hereinafter, a display apparatus according to one aspect of present invention will be described referring to FIG. 1.

FIG. 1 is a cross-sectional view of a display apparatus according to one aspect of the present invention. A display apparatus 100 according to one aspect may include a substrate 10, a device member 20 formed on the substrate 10, and a composite protection layer 30, formed on the device member 20, including a inorganic protection layer 31 and an organic protection layer 32, wherein the inorganic protection layer 31 may be formed in contact with the device member 20, and the organic protection layer 32 may be prepared of a composition for display sealing material according to aspects of the present invention.

As used herein, the display means a light emitting diode (LED), an organic light emitting diode (OLED), an light instrument, an light instrument include both OLED light instrument and LED light instrument, as well as the display apparatus used in the art.

The display apparatus may include, but not limited to, a flexible organic electroluminescent device, an organic electroluminescent device, and the like.

The substrate 10 is not particularly limited, and may include, for example, a transparent glass, plastic film, silicon or metal substrate, and the like.

The device member 20 may include, for example, an organic electroluminescent device, and include a first electrode, a second electrode, an organic emitting layer between the first electrode and the second electrode, and the organic emitting layer may be a layer in which a hole injection layer, a hole transporting layer, an emitting layer, an electron transporting layer, an electron injection layer, without limitation, are laminated sequentially.

The composite protection layer 30 may include the inorganic protection layer 31 and the organic protection layer 32, and the inorganic protection layer 31 and the organic protection layer 32 may be prepared of different components and serve individually as the encapsulant of the device member.

The inorganic protection layer 31 may have the different component from that of the organic protection layer 32, and complement the effect of the organic protection layer 32. The inorganic protection layer 31 may be prepared of the inorganic materials having excellent light transmittance and barrier property of moistures and/or oxygen. For example, the inorganic protection layer 31 may include metals, non-metals, intermetallic compounds or alloys, non-intermetallic compounds or alloys, metal or non-metal oxides, metal or non-metal fluorides, metal or non-metal nitrides, metal or non-metal carbides, metal or non-metal oxynitrides, metal or non-metal borides, metal or non-metal oxyborides, metal or non-metal silicides, or mixtures thereof. The metal may include, but not limited to, at least in of semimetals, basic metals, transition metals and lanthanide metals, specifically the metal may include at least one of silicon (Si), aluminum (Al), selenium (Se), zinc (Zn), antimony (Sb), indium (In), germanium (Ge), tin (Sn), bismuth (Bi), transition metal, lanthanide metal, and the like. Specifically, the inorganic protection layer may include silicon oxides (SiOx), silicon nitrides (SiNx), silicon oxynitrides (SiOxNy), ZnSe, ZnO, $Sb_2O_3$, AlOx such as $Al_2O_3$, and the like, $In_2O_3$, or $SnO_2$, wherein x and y are each 1 to 5.

The inorganic protection layer 31 may be deposited by a plasma process, a vacuum process, for example a sputtering, a chemical vapor deposition, a plasma-enhanced chemical vapor deposition, an evaporation, a sublimation, an electron cyclotron resonance-plasma chemical vapor deposition and combinations thereof.

The thickness of the inorganic protection layer 31 is not particularly limited but may be 100 Å to 2000 Å. Within this range, the encapsulating effect may be enhanced.

The organic protection layer 32 may be prepared by a deposition, an ink jet, a screen printing, a spin coating, a blade coating, a curing, alone or in combination thereof, of the composition for display sealing material according to aspects of the present invention. For example, the composition for display sealing material may be coated into about 1 μm to about 50 m thickness, and subjected to UV curing a dose of about 10 mW/cm$^2$ to about 500 mW/cm$^2$ for about 1 to about 100 seconds.

Having not described in FIG. 1, the organic protection layer and the inorganic protection layer may be deposited alternately into 3 or more layers. If the organic protection layer is deposited between 2 or more of inorganic protection layers, it is possible to ensure the smoothness of the inorganic protection layer, and prevent the defect of the inorganic protection layer from being transmitted to the other inorganic protection layer. In addition, if the inorganic protection layer is deposited between 2 or more of organic protection layers, it is possible to enhance or increase the effect of encapsulating the apparatus.

The composite protection layer 30 may include the inorganic protection layer 31 and the organic protection layer 32 alternately, provided that the total number of the inorganic protection layer 31 and the organic protection layer 32 is not limited. The total number of the inorganic protection layer 31 and the organic protection layer 32 may depend on the level of the permeability resistance to oxygen and/or moistures and/or water vapor and/or chemicals. For example, the total number of the inorganic protection layer 31 and the organic protection layer 32 may be 10 or less, for example, 2 to 7. Specifically, seven layers such as the inorganic protection layer/the organic protection layer/the inorganic protection layer/the organic protection layer/the inorganic protection layer/the organic protection layer/the inorganic protection layer sequentially may be formed.

The display apparatus may have the generated amount of the outgases of about 2000 ppm or less. Within this range, the display member may have long self-life and high reliability. In particularly, the amount may be about 10 ppm to about 1000 ppm.

Hereinafter, a display apparatus according to another aspect of present invention now will be described referring to FIG. 2. FIG. 2 is a cross-sectional view of a display apparatus according to another aspect of the present invention.

Referring to FIG. 2, a display apparatus 200 according to another aspect may include a substrate 10, a device member 20 formed on the substrate 10, and a composite protection layer 30, formed on the device member 20, including a inorganic protection layer 31 and an organic protection layer 32, wherein the inorganic protection layer 31 may encapsulate an internal space 40 in which the device member 20 is received, and the organic protection layer 32 may be prepared of a composition for display sealing material according to aspects of the present invention. The organic light emitting device display according to another aspect of the present invention is substantially same as the display according to one aspect of the present invention except that the inorganic protection layer 31 is not contact with the device member 20 and therefore.

MODE FOR INVENTION

Hereinafter, the present invention will be described in more detail with reference to some examples. However, it should be understood that these examples are provided for illustration only and are not to be in any way construed as limiting the present invention. A description of details apparent to those skilled in the art will be omitted for clarity.

Preparative Example 1

To a 3000 ml flask equipped with a cooling pipe and a stirrer, 300 ml of dichloromethane (Sigma-Aldrich) was charged, and 200 g of 4-hydroxybutyl acrylate (Shin-Nakamura Chemical Co., Ltd.) and 168 g of triethylamine were added. After the temperature in the flask was allowed to cool to 0° C., a solution of 278 g of p-toluene sulfonyl chloride (Sigma-Aldrich) in 500 ml of dichloromethane was dropwise added for 2 hours while stirring. Thereafter, the solution was stirred for 5 hours again and the residual solvents were removed by a distillation. Then, 300 g of the obtained compound was added to 1000 ml of acetonitrile (Sigma-Aldrich), and 220 g of potassium carbonate (Sigma-Aldrich) and 141 g of 2-phenylphenol (Sigma-Aldrich) were added while stirring at 80° C. The residual solvents and reaction residues were removed to afford a compound of formula 5 (molecular weight: 296.36) having a purity of 93% as determined by HLPC.

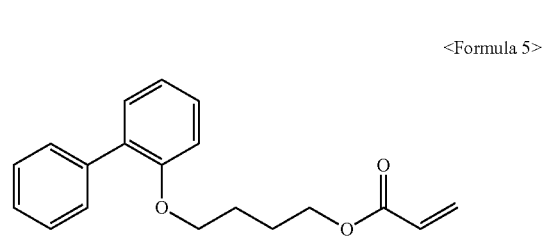 [SMILES: C=CC(=O)OCCCCOc1ccccc1-c1ccccc1]

<Formula 5>

Preparative Example 2

To a 2000 ml flask equipped with a cooling pipe and a stirrer, 600 ml of dichloromethane (manufacturer: Sigma-Aldrich) was charged, 58.8 g of hydroxyethyl methacrylate (Sigma-Aldrich) and 52.2 g of triethylamine (Sigma-Aldrich) were added while stirring at 0° C. and 100 g of triphenyl chloromethane (Sigma-Aldrich) was slowly added. After the temperature in the flask was allowed to increase to 25° C., the solution was stirred for 4 hours. Then, dichloromethane was removed by a vacuum distillation and the solution was subjected to a chromatography through a silica gel column to obtain a compound of formula 6 (124 g) having a purity of 97% as determined by HLPC.

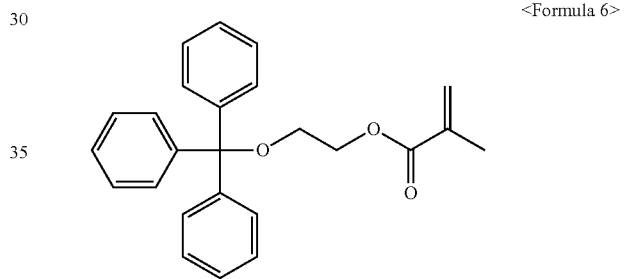

<Formula 6>

Preparative Example 3

To a 2000 ml flask equipped with a cooling pipe and a stirrer, 800 ml of acetonitrile (Fisher) was charged, 180 g of potassium carbonate (Aldrich) and 108 g of acrylic acid were added while stirring at 0° C., and 150 g of 4,4'-bis (chloromethyl) biphenyl (TCI) was slowly added. After the temperature in the flask was allowed to increase to 70° C., the solution was stirred for 12 hours. Then, acetonitrile was removed by a vacuum distillation and the solution was subjected to a chromatography through a silica gel column to obtain a compound of formula 7 (177 g) having a purity of 97% as determined by HLPC.

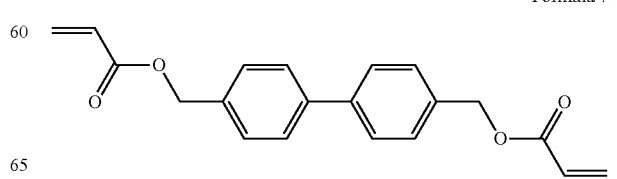

<Formula 7>

Preparative Example 4

To a 3000 ml flask equipped with a cooling pipe and a stirrer, 300 ml of dichloromethane (Sigma-Aldrich) was charged, 200 g of hydroxylethyl acrylate (Shin-Nakamura Chemical Co., Ltd.) and 168 g of trimethylamine were added. After the temperature in the flask was allowed to decrease to 0° C., the solution in which 278 g of p-toluene sulfonyl chloride (Sigma-Aldrich) was dissolved in 500 ml of dichloromethane was drop-wise added for 2 hours while stirring. After stirring for 5 hours again, the remaining solvent was removed by distillation. 300 g of the obtained compound was added to 1000 ml of acetonitrile (Sigma-Aldrich), and 220 g of potassium carbonate (Sigma-Aldrich) and 141 g of 2-phenylphonol (Sigma-Aldrich) were added again, and stirred at 80° C. Then, the remaining solvent and the reaction residues were removed to obtain a compound of formula 8 (molecular weight 296.36) having a purity of 93% as determined by HLPC.

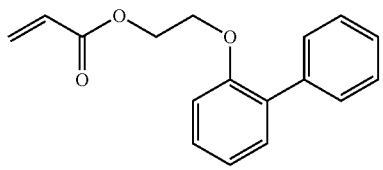

<Formula 8>

Preparative Example 5

To a 3000 ml flask equipped with a cooling pipe and a stirrer, 300 ml of dichloromethane (Sigma-Aldrich) was charged, 400 g of hydroxylethyl acrylate (Shin-Nakamura Chemical Co., Ltd.) and 168 g of trimethylamine were added. After the temperature in the flask was allowed to decrease to 0° C., the solution in which 278 g of p-toluene sulfonyl chloride (Sigma-Aldrich) was dissolved in 500 ml of dichloromethane was drop-wise added for 2 hours while stirring. After stirring for 5 hours again, the remaining solvent was removed by distillation. 300 g of the obtained compound was added to 1000 ml of acetonitrile (Sigma-Aldrich), and 220 g of potassium carbonate (Sigma-Aldrich) and 141 g of 2-phenylphonol (Sigma-Aldrich) were added again, and stirred at 80° C. Then, the remaining solvent and the reaction residues were removed to obtain a compound formula 9 (molecular weight 382.41) having a purity of 91% as determined by HLPC.

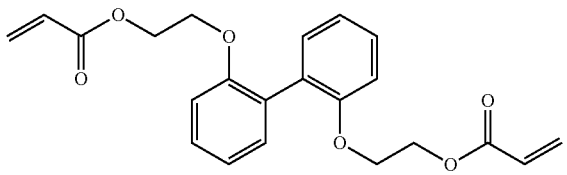

<Formula 9>

Preparative Example 6

To a 1000 ml flask equipped with a cooling pipe and a stirrer, 8.2 g of zinc perchlorate (Sigma-Aldrich) was added to 100 g of benzene thiol and 200 ml of dichloromethane (Sigma-Aldrich) while stirring, and 109.05 g of styrene oxide (Sigma-Aldrich) was drop-wise slowly added to allow the reaction to proceed at an ambient temperature. After 4 hours, the inorganic materials were removed using water and dichloromethane, and the remaining solvent was removed to obtain 192 g of a first product. To a 2000 ml flask, 150 g of the first product, 70.31 g of trimethylamine (Sigma-Aldrich) and 500 ml of dichloromethane were added and stirred at 0° C., and 64.84 g of acryloyl chloride (Sigma-Aldrich) was drop-wise slowly added to allow the reaction to proceed. After adding, the temperature was slowly increased to the ambient temperature, and the mixture was stirred for 4 hours again. After reaction, n-hexane (daejung chemicals & metals co.) was purified to remove salts and impurities, and the remaining solvent was distillated under reduced pressure to obtain a compound of formula 10 (molecular weight 284.37) having a purity of 85% as determined by HLPC.

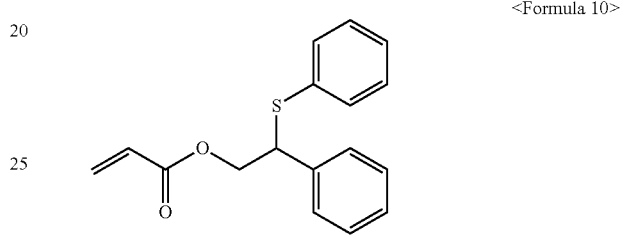

<Formula 10>

The details of components used in Examples and Comparative Examples are as follow:

(A) Monomer not containing an aromatic hydrocarbon group:
  (a1) Dodecanediol dimethacrylate (Satomer)
  (a2) Triethylene glycol dimethacrylate (BASF SE)
  (a3) Trimethylolpropane triacrylate (BASF SE)
  (a4) 2-Dimethylaminoethyl acrylate (ACROS)

(B) Monomer containing two or more of substituted or unsubstituted phenyl groups:
  (b1) Monomer of Preparative Example 1
  (b2) Monomer of Preparative Example 2
  (b3) Monomer of Preparative Example 3
  (b4) Monomer of Preparative Example 4
  (b5) Monomer of Preparative Example 5
  (b6) Monomer of Preparative Example 6
  (b7) CP-011 (4-cumylphenoxyethyl acrylate, Hannong Chemicals, Inc.)
  (b8) Bisphenol A dimethacrylate (Aldrich)
  (b9) BPM-102 (Bisphenol A ethoxylated (10) methacrylate, Hannong Chemicals, Inc.)
  (b10) Bisphenol F ethoxylated (2) diacrylate (Aldrich)

(C) Photo-initiator: phosphorus initiator (Darocur TPO, BASF SE)

Example 1

To 125 ml brown polypropylene bottle, 90 parts by weight of (a1), 10 parts by weight of (b1) and 5 parts by weight of (C) were charged, and stirred using a shaker for 3 hours to prepare a composition for display sealing material of Example 1.

Examples 2 to 25 and Comparative Examples 1 to 15

The compositions were prepared in the same manner as in Example 1 except that the kinds and amounts of the each component as shown in Tables 1 to 3 were used.

Evaluation of Physical Property (1) Plasma etching rate (%): A specimen including a 5 μm thick organic protection layer was prepared by applying the composition for display sealing material of Examples and Comparative Examples on 525±25 μm thick silicon wafer by a spray, and was subjected to UV curing at a dose of 100 mW/cm² for 10 seconds. The prepared specimen was plasma treated with an argon gas using an ICP dry etcher (Plasma lab system 133. Oxford instruments) under conditions of ICP power 2500 W, RE power 300 W, DC bias 200 V, Ar flow 50 sccm, etching time 1 min and pressure 10 mTorr. The plasma etching rate was determined by measuring the thickness (T0) of the organic protection layer before plasma treatment and the thickness (T1) of the organic protection layer after treatment and calculating the plasma etching rate according to Eq. 1, and the results thereof were shown in Tables 1 to 3:

Plasma etching rate(nm/min)=$(T0-T1)/M$ [Equation 1]

(2) Surface roughness (nm): The specimen prepared as described above in evaluation of physical property (1) was placed on an atomic force microscope (XE-100, Park systems), and a surface roughness was determined by setting a Head Mode to contact Mode, and a PSPD Display Window to A+B→1V, A-B→-500 mV to +500 mV.

(3) Color coordinate YI (ASTM D1925): Transmittance was measured on the specimen prepared as described above in evaluation of physical property (1), at a wavelength of 300 nm to 800 nm using an UV-visible spectrophotometer (UV-2450, SHIMADZU) analysis equipment followed by the calculation of a color coordinate YI (ASTM D1925).

(4) Light transmittance (%): Total transmittance was measured on the specimen prepared as described above in evaluation of physical property (1), at a wavelength of 400 to 700 nm using a hazemeter (NDH-5000, Nippon Denshoku) according to ASTM D1003-95 5.

TABLE 1

| (Unit: pbw) | | Examples | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| (A) | (a1) | 90 | 80 | 70 | 60 | 60 | 60 | — | — | — | — | — | 60 | 60 |
| | (a2) | — | — | — | — | — | — | 60 | 50 | — | — | — | — | — |
| | (a3) | — | — | — | — | — | — | 20 | — | 30 | 30 | — | — | — |
| | (a4) | — | — | — | — | — | — | — | 20 | 30 | 30 | 60 | — | — |
| (B) | (b1) | 10 | 20 | 30 | 40 | — | — | 20 | 30 | — | — | — | — | — |
| | (b2) | — | — | — | — | 40 | — | — | — | 40 | — | 20 | — | — |
| | (b3) | — | — | — | — | — | 40 | — | — | — | 40 | 20 | — | — |
| | (b4) | — | — | — | — | — | — | — | — | — | — | — | 40 | — |
| | (b5) | — | — | — | — | — | — | — | — | — | — | — | — | 40 |
| | (b6) | — | — | — | — | — | — | — | — | — | — | — | — | — |
| | (b7) | — | — | — | — | — | — | — | — | — | — | — | — | — |
| | (b8) | — | — | — | — | — | — | — | — | — | — | — | — | — |
| | (b9) | — | — | — | — | — | — | — | — | — | — | — | — | — |
| | (b10) | — | — | — | — | — | — | — | — | — | — | — | — | — |
| (C) | | 5 | 5 | 5 | 5 | 5 | 5 | 5 | 5 | 5 | 5 | 5 | 5 | 5 |
| Plasma etching rate (nm/min) | | 385 | 364 | 357 | 331 | 328 | 342 | 353 | 341 | 320 | 336 | 326 | 325 | 342 |
| Surface roughness | | 1.24 | 1.33 | 1.52 | 1.83 | 1.86 | 1.65 | 1.44 | 1.64 | 1.87 | 1.73 | 1.74 | 1.83 | 1.54 |
| Color coordinate YI | | 0.41 | 0.41 | 0.41 | 0.41 | 0.4 | 0.42 | 0.41 | 0.41 | 0.42 | 0.42 | 0.41 | 0.41 | 0.41 |
| Light transmittance (%) | | 99 | 99 | 99 | 99 | 99 | 99 | 99 | 99 | 99 | 99 | 99 | 99 | 99 |

TABLE 2

| (Unit: pbw) | | Examples | | | | | | | | | | | |
|---|---|---|---|---|---|---|---|---|---|---|---|---|---|
| | | 14 | 15 | 16 | 17 | 18 | 19 | 20 | 21 | 22 | 23 | 24 | 25 |
| (A) | (a1) | 60 | — | — | — | — | — | 60 | 60 | 60 | 60 | — | — |
| | (a2) | — | 50 | — | 60 | — | 30 | — | — | — | — | 70 | — |
| | (a3) | — | — | 30 | — | 70 | — | — | — | — | — | — | 70 |
| | (a4) | — | 20 | 30 | — | — | 30 | — | — | — | — | — | — |
| (B) | (b1) | — | — | — | — | — | — | — | — | — | — | — | 20 |
| | (b2) | — | — | — | — | — | — | — | — | — | — | — | — |
| | (b3) | — | — | — | 20 | — | — | — | — | — | — | — | — |
| | (b4) | — | 30 | — | — | 20 | — | 35 | 35 | 35 | 35 | — | — |
| | (b5) | — | — | 40 | 20 | — | 20 | — | — | — | — | 20 | — |
| | (b6) | 40 | — | — | — | 10 | 20 | — | — | — | — | — | — |
| | (b7) | — | — | — | — | — | — | 5 | — | — | — | — | — |
| | (b8) | — | — | — | — | — | — | — | 5 | — | — | 10 | — |
| | (b9) | — | — | — | — | — | — | — | — | 5 | — | — | — |
| | (b10) | — | — | — | — | — | — | — | — | — | 5 | — | 10 |
| (C) | | 5 | 5 | 5 | 5 | 5 | 5 | 5 | 5 | 5 | 5 | 5 | 5 |
| Plasma etching rate (nm/min) | | 360 | 340 | 335 | 338 | 348 | 328 | 323 | 320 | 320 | 321 | 354 | 352 |
| Surface roughness | | 1.74 | 1.64 | 1.68 | 1.53 | 1.74 | 1.52 | 1.83 | 1.82 | 1.83 | 1.82 | 1.63 | 1.64 |
| Color coordinate YI | | 0.43 | 0.42 | 0.41 | 0.41 | 0.42 | 0.42 | 0.42 | 0.42 | 0.42 | 0.42 | 0.42 | 0.42 |
| Light transmittance (%) | | 100 | 99 | 99 | 99 | 99 | 99 | 99 | 99 | 99 | 99 | 99 | 99 |

TABLE 3

| (Unit: pbw) | | Comparative Examples | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| (A) | (a1) | 100 | 50 | 60 | 95 | — | — | — | — | — | — | 50 | — | — | 30 | — |
| | (a2) | — | — | 40 | — | 40 | — | — | 50 | — | — | — | — | 30 | — | — |
| | (a3) | — | — | — | 5 | — | 20 | — | — | 30 | — | — | 50 | — | — | 50 |
| | (a4) | — | — | — | — | — | 20 | 40 | — | — | 40 | — | — | 20 | 20 | — |
| (B) | (b1) | — | 50 | — | — | 60 | — | — | — | — | — | — | — | — | — | 30 |
| | (b2) | — | — | — | — | — | — | 30 | 20 | — | — | — | — | — | — | — |
| | (b3) | — | — | — | — | — | 60 | 30 | — | — | — | — | — | — | — | — |
| | (b4) | — | — | — | — | — | — | — | 30 | 40 | — | — | — | — | — | — |
| | (b5) | — | — | — | — | — | — | — | — | 30 | 30 | — | — | 30 | — | — |
| | (b6) | — | — | — | — | — | — | — | — | — | 30 | — | 30 | — | 30 | — |
| | (b7) | — | — | — | — | — | — | — | — | — | — | 50 | 20 | — | — | — |
| | (b8) | — | — | — | — | — | — | — | — | — | — | — | — | 20 | — | — |
| | (b9) | — | — | — | — | — | — | — | — | — | — | — | — | — | — | 20 |
| | (b10) | — | — | — | — | — | — | — | — | — | — | — | — | — | 20 | — |
| (C) | | 5 | 5 | 5 | 5 | 5 | 5 | 5 | 5 | 5 | 5 | 5 | 5 | 5 | 5 | 5 |
| Plasma etching rate (nm/min) | | 418 | 327 | 610 | 820 | 280 | 314 | 308 | 312 | 296 | 310 | 324 | 318 | 287 | 320 | 322 |
| Surface roughness | | 1.14 | 2.16 | 1.24 | 1.22 | 3.42 | 2.43 | 3.13 | 2.24 | 3.35 | 3.14 | 2.54 | 2.43 | 3.65 | 2.44 | 2.42 |
| Color coordinate YI | | 0.41 | 0.41 | 0.41 | 0.41 | 0.45 | 0.46 | 0.44 | 0.41 | 0.41 | 0.43 | 0.46 | 0.45 | 0.48 | 0.45 | 0.45 |
| Light transmittance (%) | | 99 | 99 | 99 | 99 | 99 | 99 | 99 | 99 | 99 | 100 | 99 | 99 | 95 | 99 | 99 |

In the result of Tables 1 to 3, it is shown that the composition had low plasma etching rate and thus remarkably excellent plasma resistance, and a surface roughness value of 2 nm or less and thus excellent smoothness in Examples. Further, it is apparent that the composition had color coordinate YI (ASTM D1925) of less than 0.50 and high light transmittance, thus providing the transparent organic protection layer. Meanwhile, there were problems such as high etching rate and surface roughness in Comparative Examples relative Examples.

Many modifications and other embodiments of the present invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims.

The invention claimed is:

1. A composition for display sealing material, the composition comprising a photo-curable monomer and a photopolymerization initiator,
wherein:
the photo-curable monomer includes a first monomer and a second monomer, the first monomer not containing an aromatic hydrocarbon group and not containing a C3 to C20 cycloalkyl group; and the second monomer containing two or more of substituted or unsubstituted phenyl groups, represented by Formula 1,
the first monomer includes at least one of a mono(meth) acrylate having an amine group, a di(meth)acrylate having a substituted or unsubstituted C1 to C20 alkylene group that does not include a C2 to C30 heterocycloalkyl group, a di(meth)acrylate having an ethylene oxide group, and a tri(meth)acrylate having an ethylene oxide group, and
the second monomer is present in an amount of from about 10 wt % to about 40 wt % in the photo-curable monomer, and the first monomer is present in an amount of from about 60 wt % to about 90 wt % in the photo-curable monomer:

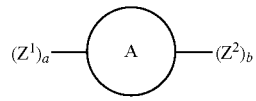

<Formula 1> wherein, in Formula 1,

A is a hydrocarbon having two or more of substituted or unsubstituted phenyl groups, or a hydrocarbon having a heteroatom and two or more of substituted or unsubstituted phenyl groups;

$Z^1$ and $Z^2$ are each independently represented by Formula 2; and a and b are an inter of 0 to 2, respectively, and a+b is an inter of 1 to 4;

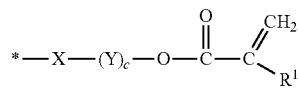

<Formula 2> wherein, in Formula 2,

* represents a linker site to a carbon atom on A;

X is a single bond, O, or S;

Y is a substituted or unsubstituted C1 to C10 linear alkylene group, or a substituted or unsubstituted C1 to C20 alkoxy group, $R^1$ is a hydrogen or a C1 to C5 alkyl group; and c is 0 or 1.

2. The composition for display sealing material according to claim 1, wherein the second monomer includes at least one of a mono(meth)acrylate and a di(meth) acrylate.

3. The composition for display sealing material according to claim 2, wherein:
the second monomer includes the mono(meth)acrylate, and the mono(meth)acrylate is represented by Formula 3:

<Formula 3>

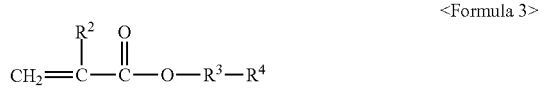

wherein, in Formula 3, $R^2$ is hydrogen or a methyl group, $R^3$ is a substituted or unsubstituted linear C1 to C10 alkylene group, or a substituted or unsubstituted C1 to C20 alkoxy group, and $R^4$ is a hydrocarbon having two or more of substituted or unsubstituted phenyl groups, or a hydrocarbon having a heteroatom and two or more of substituted or unsubstituted phenyl groups.

4. The composition for display sealing material according to claim 2, wherein:
the second monomer includes the di(meth)acrylate, and the di(meth) acrylate is represented by Formula 4:

<Formula 4>

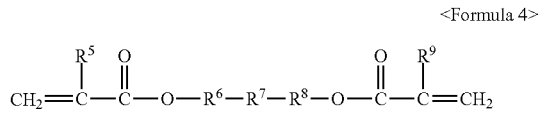

wherein, in Formula 4, $R^5$ and $R^9$ are hydrogen or a methyl group, $R^6$ and $R^8$ are each independently a substituted or unsubstituted linear C1 to C10 alkylene group, or a substituted or unsubstituted C1 to C20 alkoxy group, and $R^7$ is a hydrocarbon having two or more of substituted or unsubstituted phenyl groups, or a hydrocarbon having a heteroatom and two or more of substituted or unsubstituted phenyl groups.

5. The composition for display sealing material according to claim 1, wherein the second monomer includes at least one of 4-(meth)acryloxy-2-hydroxybenzophenone, ethyl-3,3-diphenyl(meth)acrylate, benzoyloxyphenyl (meth)acrylate, bisphenol A di(meth)acrylate, ethoxylated bisphenol A di(meth)acrylate, bisphenol F di(meth)acrylate, ethoxylated bisphenol F di(meth)acrylate, 4-cumylphenoxyethylacrylate, 2-phenylphenoxyethyl (meth)acrylate, 2,2'-phenylphenoxyethyl di(meth)acrylate, 2-phenylphenoxypropyl(meth)acrylate, 2,2'-phenylphenoxypropyl di(meth)acrylate, 2-phenylphenoxybutyl(meth)acrylate, 2,2'-phenylphenoxybutyl di(meth)acrylate, 2-(3-phenylphenyl)ethyl (meth)acrylate, 2-(4-benzylphenyl)ethyl (meth)acrylate, 2-phenyl-2-(phenylthio)ethyl (meth)acrylate, 2-(triphenylmethyloxy)ethyl (meth)acrylate, 4-(triphenylmethyloxy)butyl(meth) acrylate, 3-(biphenyl-2-yloxy)butyl(meth)acrylate, 2-(biphenyl-2-yloxy)butyl(meth)acrylate, 4-(biphenyl-2-yloxy)propyl(meth)acrylate, 3-(biphenyl-2-yloxy)propyl (meth)acrylate, 2-(biphenyl-2-yloxy)propyl(meth)acrylate, 4-(biphenyl-2-yloxy)ethyl(meth)acrylate, 3-(biphenyl-2-yloxy)ethyl (meth)acrylate, 2-(4-benzylphenyl)ethyl(meth) acrylate, 4,4'-di(acryloyloxymethyl)biphenyl, 2,2'-di(acryloyloxyethoxy)biphenyl, structural isomers thereof, or mixtures thereof.

6. The composition for display sealing material according to claim 1, wherein the hydrocarbon having two or more of phenyl groups, or a hydrocarbon having a heteroatom and two or more of substituted or unsubstituted phenyl groups includes a substituted or unsubstituted biphenyl group, a substituted or unsubstituted triphenylmethyl group, a substituted or unsubstituted terphenyl group, a substituted or unsubstituted biphenylene group, a substituted or unsubstituted terphenylene group, a substituted or unsubstituted quaterphenylene group, a substituted or unsubstituted 2-phenyl-2-(phenylthio)ethyl group, a substituted or unsubstituted 2,2-diphenylpropane group, a substituted or unsubstituted diphenylmethane group, a substituted or unsubstituted cumyl phenyl group, a substituted or unsubstituted bisphenol F group, a substituted or unsubstituted bisphenol A group, a substituted or unsubstituted biphenyloxy group, a substituted or unsubstituted terphenyloxy group, a substituted or unsubstituted quaterphenyloxy group, a substituted or unsubstituted quinquephenyloxy group, and the like.

7. The composition for display sealing material according to claim 1, wherein the second monomer has a weight average molecular weight of about 100 g/mol to about 1000 g/mol or less.

8. The composition for display sealing material according to claim 1, wherein the photo-curable monomer is consisted of only an element selected from C, H, O, N and S.

9. The composition for display sealing material according to claim 1, wherein the photopolymerization initiator is at least one of triazine, acetophenone, benzophenone, thioxanthone, benzoin, phosphorus, and oxime initiator.

10. The composition for display sealing material according to claim 1, further including a thermal stabilizer.

11. The composition for display sealing material according to claim 10, wherein the thermal stabilizer is present in an amount of about 100 ppm to about 1000 ppm, on the solid contents, in the composition for display sealing material.

12. A display apparatus including:
a display member; and
a composite protection layer formed on the display member,
wherein:
the composite protection layer includes a inorganic protection layer and an organic protection layer, and
the organic protection layer includes a cured product prepared of the composition for display sealing material according to claim 1.

13. The display apparatus according to claim 12, wherein:
the inorganic protection layer includes at least one selected from metal, oxides of the metal, fluorides of the metal, nitrides of the metal, oxynitrides of the metal, borides of the metal, oxyborides of the metal, and silicides of the metal, and
the metal includes at least one selected from silicon (Si), aluminum (Al), selenium (Se), zinc (Zn), antimony (Sb), indium (In), germanium (Ge), tin (Sn), bismuth (Bi), transition metal, and lanthanide metal.

14. The display apparatus according to claim 12, wherein the display member is a light emitting diode (LED), an organic light emitting diode (OLED), an OLED light instrument or a LED light instrument.

15. The composition for display sealing material according to claim 1, wherein the first monomer includes 2-aminoethyl (meth)acrylate, 2-dimethylaminoethyl (meth)acrylate, octanediol di(meth)acrylate, nonanediol di(meth)acrylate, decanediol di(meth)acrylate, undecanediol di(meth)acrylate, dodecanediol di(meth)acrylate, ethylene glycol di(meth)acrylate, triethylene glycol di(meth)acrylate, trimethylolpropane tri(meth)acrylate, or mixtures thereof.

* * * * *